United States Patent [19]
Wenstrom, Jr.

[11] Patent Number: 5,911,714
[45] Date of Patent: Jun. 15, 1999

[54] SURGICAL CANNULA SYSTEM

[75] Inventor: Richard F. Wenstrom, Jr., Attleboro, Mass.

[73] Assignee: Mitek Surgical Products, Inc., Westwood, Mass.

[21] Appl. No.: 08/610,623

[22] Filed: Mar. 4, 1996

Related U.S. Application Data

[62] Division of application No. 08/200,758, Feb. 23, 1994, Pat. No. 5,496,289.

[51] Int. Cl.⁶ ................................................. A61M 31/00
[52] U.S. Cl. .......................................... 604/506; 604/164
[58] Field of Search ................................... 604/158, 164, 604/167, 171, 264, 272, 506, 508; 128/898

[56] References Cited

U.S. PATENT DOCUMENTS

| | | | |
|---|---|---|---|
| 5,248,298 | 9/1993 | Bedi et al. | 604/264 X |
| 5,350,362 | 9/1994 | Stouder, Jr. | 604/167 |
| 5,352,206 | 10/1994 | Cushieri et al. | 604/264 X |
| 5,364,372 | 11/1994 | Danks et al. | 604/264 |
| 5,437,643 | 8/1995 | Transue | 604/164 |
| 5,453,094 | 9/1995 | Metcalf et al. | 604/164 |

*Primary Examiner*—Ronald Stright
*Assistant Examiner*—A. T. Nguyen
*Attorney, Agent, or Firm*—Pandiscio & Pandiscio

[57] ABSTRACT

A novel surgical cannula system is disclosed. The system generally comprises a guide rod, a cannula housing, an obturator and a dam assembly. A novel method for deploying the surgical cannula is also disclosed.

2 Claims, 18 Drawing Sheets

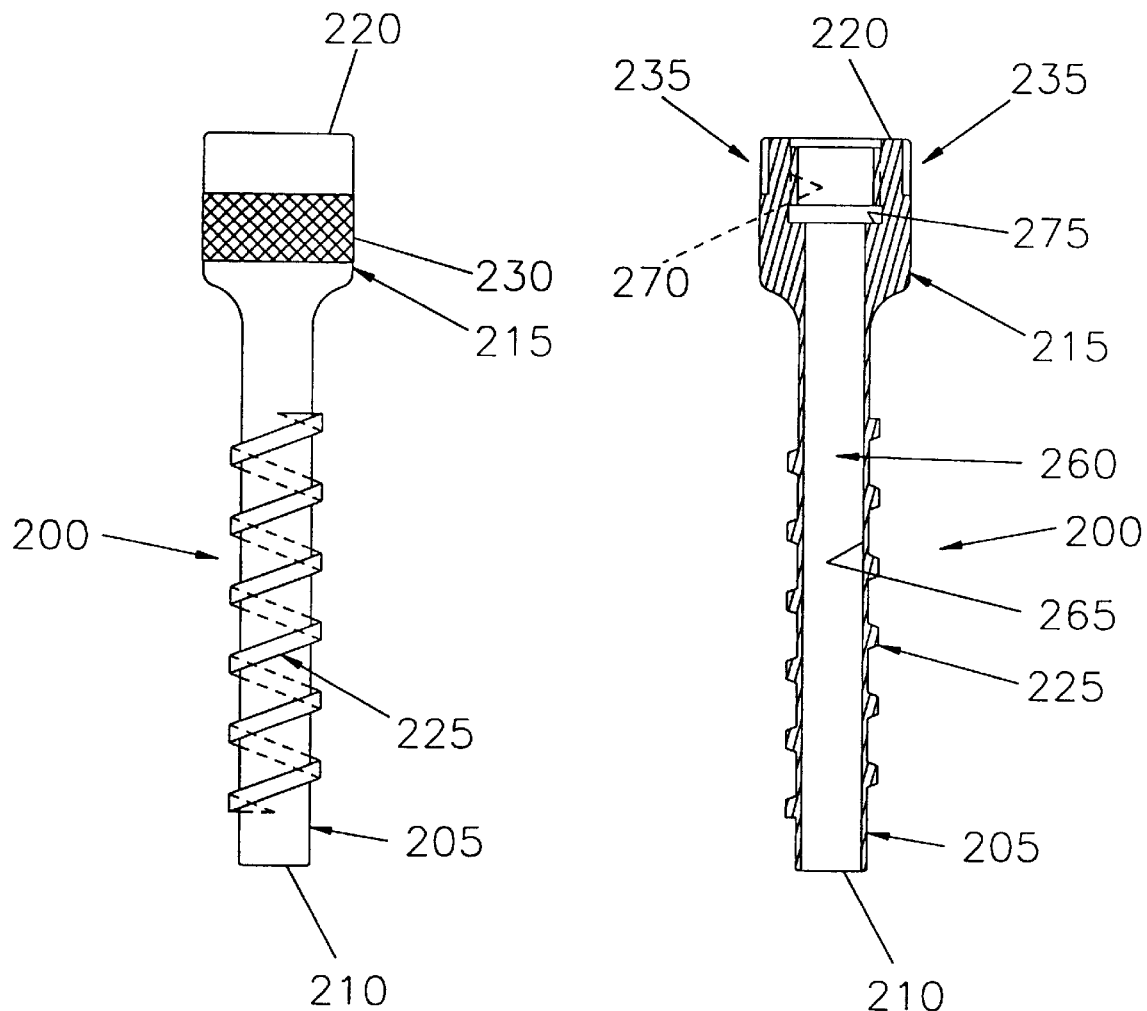
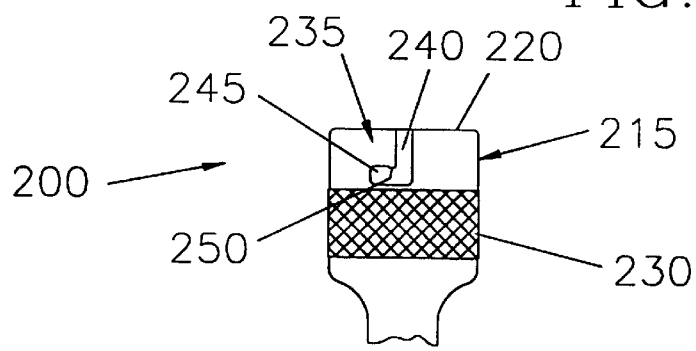

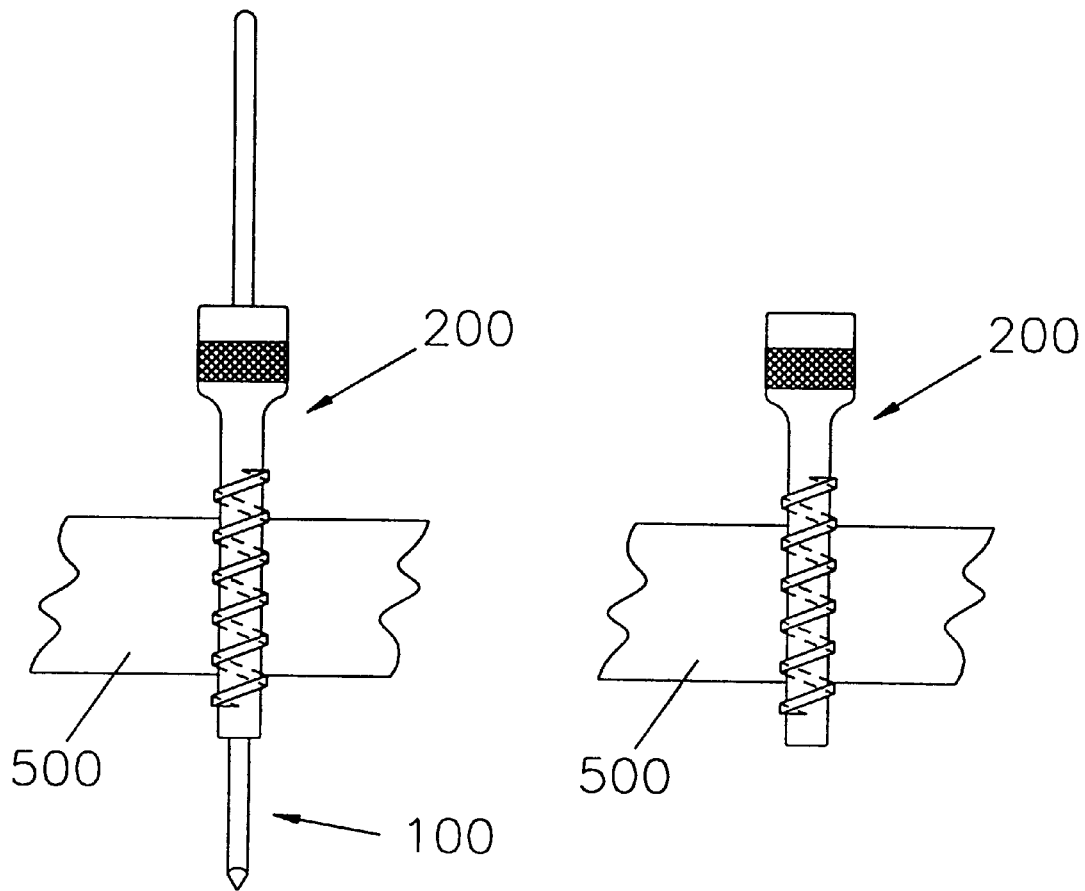

SURGICAL CANNULA SYSTEM

This is a division of U.S. patent application Ser. No. 08/200,758, filed Feb. 23, 1994 by Richard F. Wenstrom, Jr. for SURGICAL CANNULA SYSTEM now U.S. Pat. No. 5,496,289.

FIELD OF THE INVENTION

This invention relates to surgical instruments in general, and more particularly to surgical cannulae.

BACKGROUND OF THE INVENTION

Surgical cannulae are well known in the art. Such devices generally comprise tube-like members which are inserted into openings made in the body so as to line the openings and maintain them against closure. Surgical cannulae can be used for a wide variety of purposes, and their particular construction tends to vary accordingly.

For example, some surgical cannulae are designed to serve as an irrigation passageway between the surgical site and the region outside the body. In this case, these surgical cannulae (which are sometimes referred to as "irrigation cannulae") may be little more than a hollow tube, with or without an associated stopcock.

Other surgical cannulae are designed to serve as a protective liner for the surgical opening. These surgical cannulae (which are sometimes referred to as "instrument cannulae") are used to minimize tissue trauma during the insertion, use and withdrawal of surgical instruments to and from the surgical site. Since the surgical site is typically inflated and/or irrigated with a fluid during the surgical procedure (i.e., with a liquid during arthroscopic surgery and with a gas during laparoscopic surgery), these cannulae typically include some sort of fluid seal across their central opening. This fluid seal acts to minimize fluid loss from the surgical site through the cannula. Such fluid seals typically comprise one or more soft rubber disks which extend across the cannula's central opening. These disks typically have holes or slits at their center to allow surgical instruments to pass through the fluid seal and reach the surgical site.

Prior art instrument cannulae are traditionally sold as pre-assembled and pre-sterilized units which are ready for use right out of the package. In addition, these cannulae are generally made so as to be disposable at the end of the surgical procedure. To this end, prior art instrument cannulae are typically provided with their fluid seals already assembled to the cannula housings. Since prior art instrument cannulas are intended to be discarded at the end of each procedure, their housings are generally formed out of a relatively inexpensive material such as plastic.

Prior art cannulae of the sort described above tend to suffer from a number of disadvantages.

For example, the plastic housings tend to become very slippery when wet. As a result, the cannulae can sometimes slip out of position during a surgical procedure, particularly as instruments are being passed into and out of the cannula during use.

Additionally, it is generally necessary to insert a sharp-pointed trocar into the interior passageway of the cannula during cannula insertion. This sharp-pointed trocar projects out the distal end of the cannula and serves to part the patient's tissue before the advancing cannula, as well as to prevent the cannula housing from coring the tissue during cannula insertion. Unfortunately, this sharp-pointed trocar must also be pushed through the cannula's fluid seal in order to project its sharp point out the distal end of the cannula housing. The cannula's fluid seal can be damaged by the sharp tip of the trocar as the trocar passes through the fluid seal.

Furthermore, the use of fully disposable surgical cannulae can be relatively expensive when considered in the context of the total number of cannulae used in minimally invasive surgical procedures.

It has been recognized that substantial cost savings could be achieved if some or all of the instrument cannula could be reused at the conclusion of the surgical procedure. In addition, the problem of disposing of the surgical cannula after use could also be reduced.

Unfortunately, existing surgical cannulae do not lend themselves to reuse.

For one thing, the plastic used to form the cannula housings tends to be relatively soft. As a result, the inside of the cannula housing is frequently scarred during use as sharp instruments pass back and forth through the cannula. Reuse of the same housing in subsequent surgical procedures would increase this scarring problem and could lead to small pieces of plastic becoming detached from the cannula housing and entering the patient's body.

For another thing, the fluid seal used in the cannula also tends to be scarred during use. Reusing the same fluid seal in subsequent surgical procedures could compromise the fluid seal's ability to minimize fluid loss through the cannula. In addition, reusing the fluid seals in subsequent surgical procedures would increase the scarring problem and could lead to small pieces of rubber coming loose from the fluid seal and entering the patient's body.

Furthermore, existing surgical cannulae do not provide a fast and convenient way for medical personnel to recycle only a portion of a used surgical cannula. For example, existing surgical cannulae do not provide a fast and convenient way to attach a new fluid seal to a recycled cannula housing.

OBJECTS OF THE PRESENT INVENTION

Accordingly, one object of the present invention is to provide a new surgical cannula wherein at least a portion of the cannula is intended to be safely reused in a subsequent surgical procedure.

Another object of the present invention is to provide a new surgical cannula wherein the cannula's housing is constructed so as to be safely reused in a subsequent surgical procedure, and the cannula's fluid seal is intended to be discarded at the end of each surgical procedure.

Still another object of the present invention is to provide a new surgical cannula wherein medical personnel can quickly and easily attach a new fluid seal to an existing cannula housing.

Yet another object of the present invention is to provide a new surgical cannula which is simple and inexpensive to manufacture.

And another object of the present invention is to provide an improved cannula system for forming an opening in a patient's body and maintaining that opening against premature closure.

Still another object of the present invention is to provide a novel surgical cannula system comprising a guide rod, a cannula housing, an obturator adapted for selective use with the cannula housing, and a dam assembly adapted for selective use with the cannula housing.

Yet another object of the present invention is to provide an improved fluid seal for attachment to a cannula housing.

And another object of the present invention is to provide an improved obturator for use with a cannula housing.

Still another object of the present invention is to provide an improved cannula system wherein the cannula's fluid seal is not joined to the cannula housing until after the cannula housing has been positioned in the patient, in order to eliminate any possibility of damaging the cannula's fluid seal during cannula insertion.

Yet another object of the present invention is to provide a new method for forming an opening in a patient's body and maintaining that opening against premature closure.

SUMMARY OF THE INVENTION

These and other objects are achieved through the provision and use of the present invention, which comprises a novel surgical cannula system. The novel surgical cannula system generally comprises a guide rod, a cannula housing, an obturator and a dam assembly.

The guide rod comprises a shaft having a distal end and a proximal end. The distal end of the guide rod is preferably pointed.

The cannula housing comprises a distal end and a proximal end, with a central passageway extending therebetween. The cannula housing further comprises tissue locking means on its exterior surface. The cannula housing also comprises first and second mount receiving means.

The obturator comprises a shaft having a distal end and a proximal end, with a central passageway extending therebetween. The obturator further comprises first mounting means. The obturator's first mounting means cooperate with the cannula housing's first mount receiving means to releasably attach the obturator to the cannula housing after the obturator's shaft has been inserted into the cannula housing's passageway. The obturator and the cannula are sized so that the distal end of the obturator will project out the distal end of the cannula housing when the obturator's first mounting means are in operative engagement with the cannula housing's first mount receiving means.

The dam assembly comprises a housing and sealing means. The dam assembly further comprises second mounting means. The dam assembly's second mounting means cooperate with the cannula housing's second mount receiving means for sealably mounting the dam assembly to the cannula housing. The dam assembly further comprises suture holding means.

The novel surgical cannula system of the present invention is used as follows. First, the guide rod is inserted into the patient so that the distal end thereof is located at an interior surgical site, the proximal end thereof is located outside the patient, and the shaft extends through all of the intervening tissue.

Next, the obturator is assembled to the cannula housing by first inserting the obturator into the cannula housing's central passageway so as to cause the obturator's first mounting means to operatively engage the cannula housing's first mount receiving means, thereby releasably attaching the obturator to the cannula housing. As this occurs, the obturator's distal end will project out of the distal end of the cannula housing, and the obturator's proximal end will project out of the cannula housing's proximal end. The surgeon then fits this assembly over the proximal end of the guide rod and slides the assembly down the guide rod as a unit until the obturator's distal end comes into engagement with the tissue.

Next, the surgeon forces the assembly through the tissue, so that the distal end of the assembly penetrates the tissue and the cannula housing's tissue locking means securely engage the tissue. The obturator is then detached from the cannula housing and withdrawn from the cannula housing and the guide rod. The guide rod is then removed from the patient, leaving only the cannula housing extending through the tissue.

Next, the dam assembly is assembled to the cannula housing by bringing the dam assembly against the cannula housing so that the dam assembly's second mounting means operatively engage the cannula housing's second mounting means. The cannula is then ready for use by the surgeon.

During such use, the interior surgical site will typically be inflated and/or irrigated with a fluid. This fluid will be inhibited from leaving the surgical site by the sealing means. Furthermore, any sutures extending through the cannula may have their proximal ends held separate and distinct from one another by the suture holding means.

BRIEF DESCRIPTION OF THE DRAWINGS

Still other objects and features of the present invention will be more fully disclosed or rendered obvious by the following detailed description of the preferred embodiment of the invention, which is to be considered together with the accompanying drawings wherein:

FIG. 2 is a side view of the cannula housing;

FIG. 3 is a side view, in section, of the cannula housing;

FIG. 4 is a side view of the proximal portion of the cannula housing, where the cannula housing has been rotated 90° about its longitudinal axis from the position shown in FIG. 2;

FIG. 32 is a view like that of FIG. 31, except that the obturator has been withdrawn from the cannula housing and the guide rod;

FIG. 33 is a view like that of FIG. 32, except that the guide rod has been withdrawn from the cannula housing;

DETAILED DESCRIPTION OF THE PREFERRED EMBODIMENT

The present invention comprises the provision and use of a novel surgical cannula system. The novel surgical cannula system generally comprises a guide rod 100 (see FIG. 1), a cannula housing 200 (see FIGS. 2–4), an obturator 300 (see FIG. 5), and a dam assembly 400 (see FIGS. 8–12).

Figure 1:
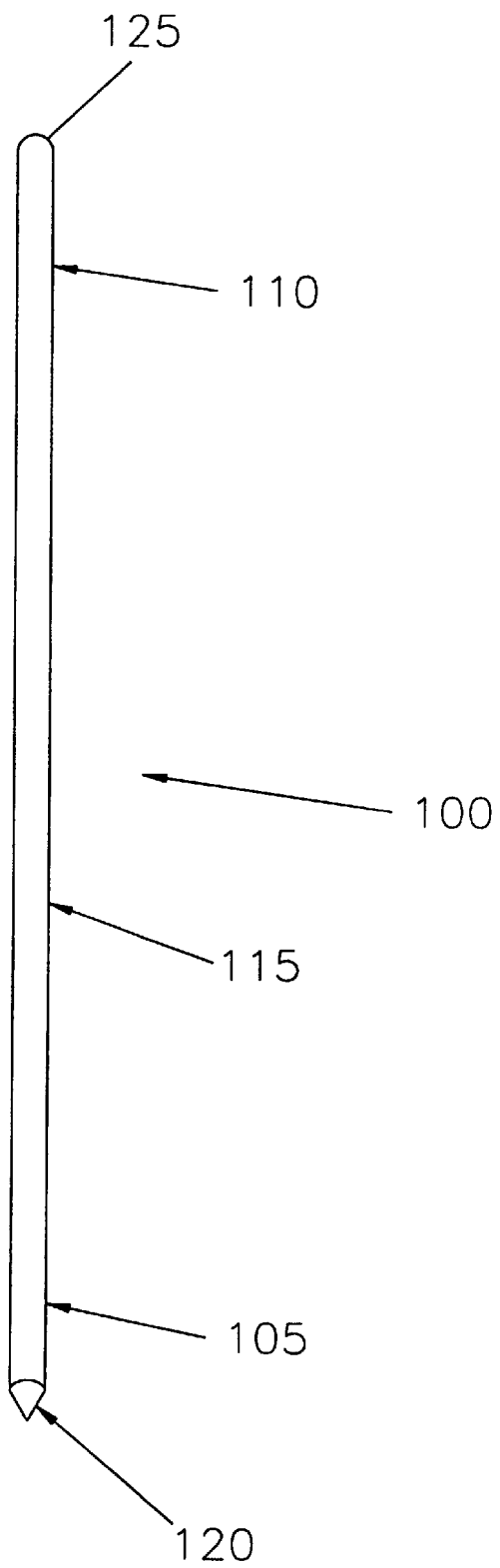
FIG. 1 is a side view of the guide rod.

Looking now at FIG. 1, guide rod 100 generally comprises a distal portion 105, a proximal portion 110, and a shaft 115 extending therebetween. Distal portion 105 terminates in a sharp point 120. Proximal portion 110 terminates in a rounded end 125. The guide rod's shaft 115 is formed with a constant diameter.

Looking next at FIGS. 2–4, cannula housing 200 generally comprises a distal portion 205 terminating in an annular distal end surface 210, and a proximal portion 215 terminating in an annular proximal end surface 220. Preferably proximal portion 215 has a larger outside diameter than distal portion 205, in the manner shown in the drawings. A helical thread 225 is formed on the outer surface of distal portion 205. Preferably helical thread 225 starts proximally of distal end surface 210 and terminates distally of proximal portion 215. A knurled section 230 is formed on the outer surface of proximal portion 215. Two L-shaped grooves 235 are formed in the outer surface of proximal portion 215. These L-shaped grooves 235 are diametrically opposed from one another. Each of the L-shaped grooves 235 comprises a longitudinally extending length 240 and a circumferentially extending length 245. Longitudinally extending length 240 opens on proximal end surface 220. A lip 250 projects into each of the circumferentially extending lengths 245, as shown in FIG. 4.

A central passageway 260 extends axially through cannula housing 200. More particularly, central passageway 260 extends between distal end surface 210 and proximal end surface 220, and comprises a bore 265 and a threaded counterbore 270. Bore 265 and threaded counterbore 270 are coaxial with one another and meet at an annular shoulder 275 which is located within the housing's proximal portion 215.

Figure 5:
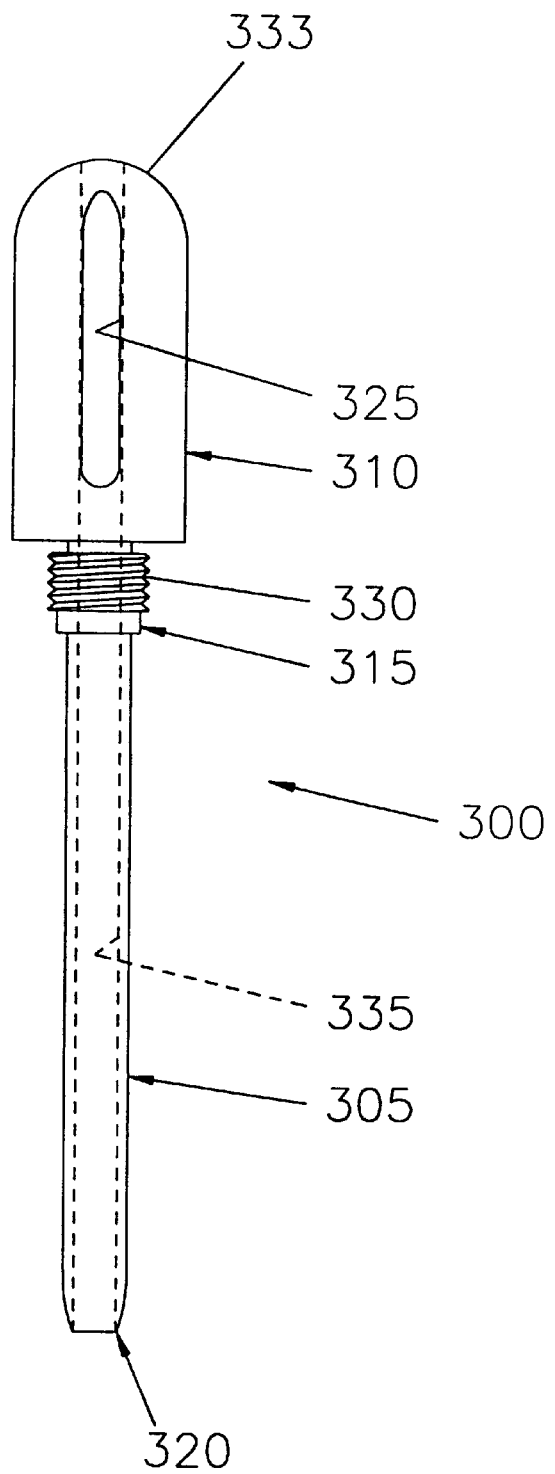
FIG. 5 is a side view of the obturator.

Looking next at FIG. 5, obturator 300 comprises a distal portion 305, a proximal portion 310, and an intermediate portion 315 connecting distal portion 305 to proximal portion 310. Distal portion 305 terminates in a substantially frustoconical distal tip 320. Proximal portion 310 serves as the obturator's handle, and to this end the outer surface of the proximal portion is preferably relieved with a plurality of parallel surface grooves 325 (only one of which is shown in the drawings) so as to enhance gripping the handle. The proximal portion of the obturator terminates in a rounded proximal end surface 333. Rounded proximal end surface 333 permits a surgeon to comfortably push the obturator in a distal direction. The obturator's intermediate portion 315 includes a helical thread 330. A central passageway 335 extends the length of the obturator, opening on both the frustoconical tip 320 and the rounded proximal end surface 333.

Figure 6:
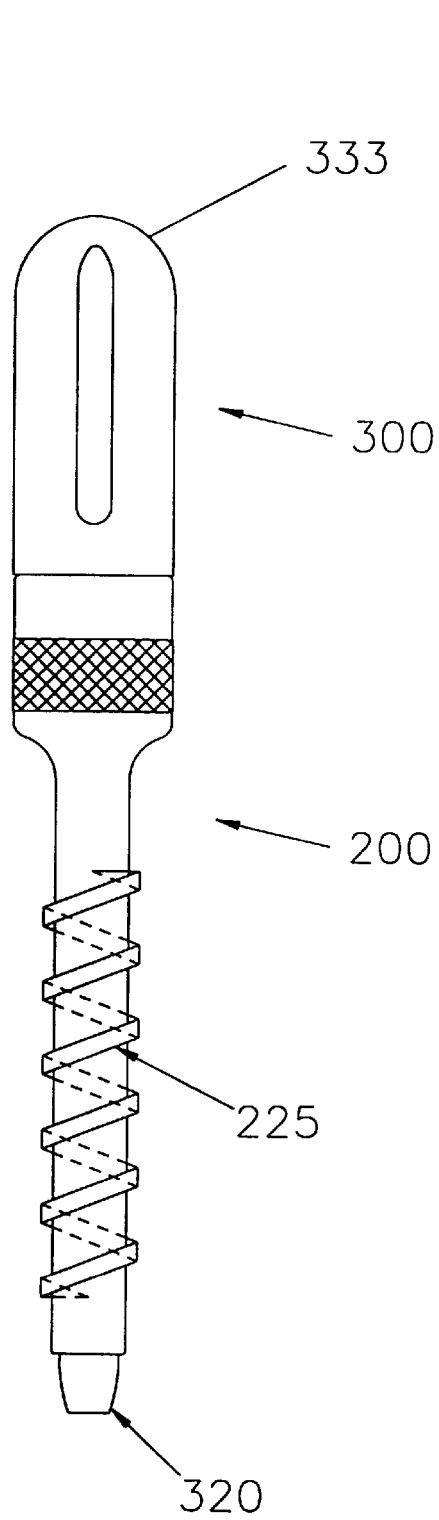
FIG. 6 is a side view showing the obturator joined with the cannula housing.

Obturator 300 is sized so that it can be received by and mate with cannula housing 200, and so that it can slide on guide rod 100. More particularly, obturator 300 is sized so that (i) its distal portion 305 can make a sliding fit within the cannula housing's central passageway 260, and (ii) its helical thread 330 can securely engage the cannula housing's threaded counterbore 270. On account of this construction, obturator 300 can be inserted distal end first into the proximal end of the cannula housing's central passageway 260, then slid down the passageway until the obturator's helical thread 330 engages the cannula housing's threaded counterbore 270, and finally screwed into position so that the obturator's proximal portion 310 engages the cannula housing's proximal portion 215. At this point obturator 300 will be securely locked to cannula housing 200, with the obturator's frustoconical distal tip 320 protruding beyond the cannula housing's distal end surface 210 (see FIG. 6). Obturator 300 may be detached from cannula housing 200 by reversing the foregoing procedure.

Figure 7:
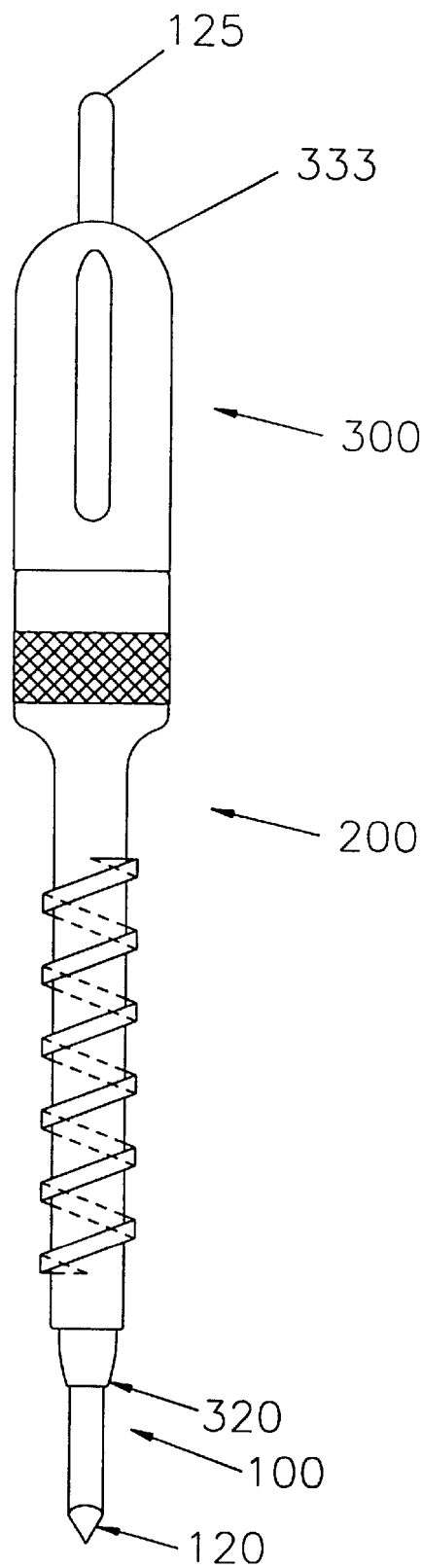
FIG. 7 is a side view showing the assembly of FIG. 6 mounted on the guide rod.
Figure 8:
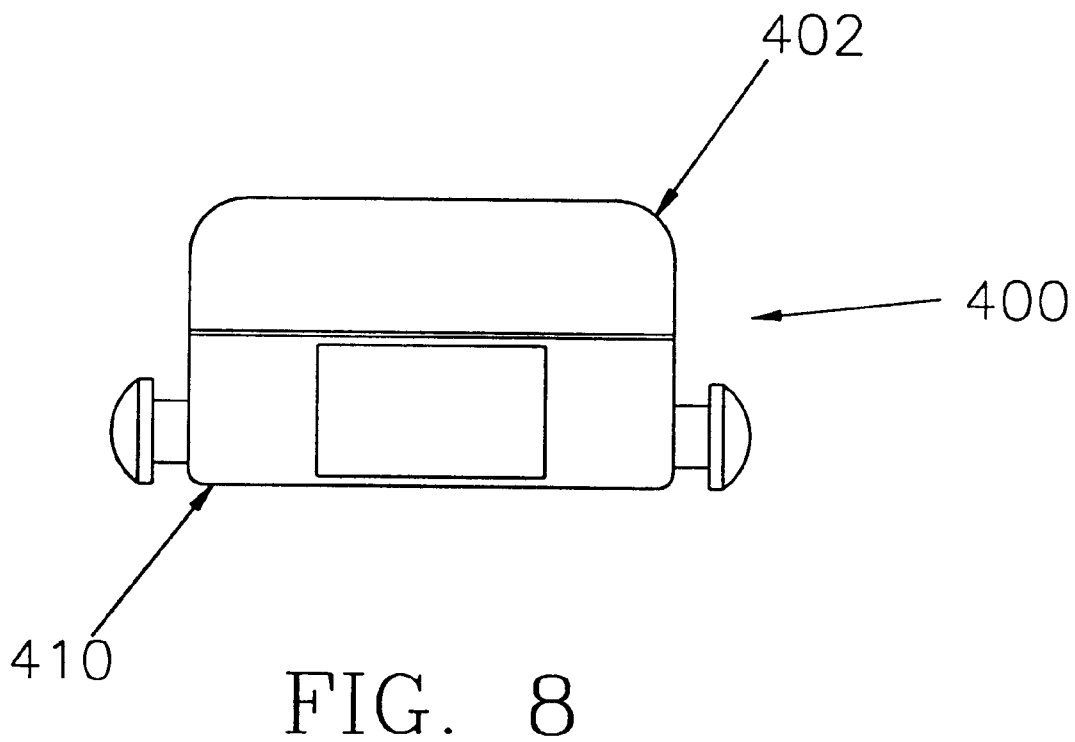
FIG. 8 is a side view of the dam assembly.
Figure 9:
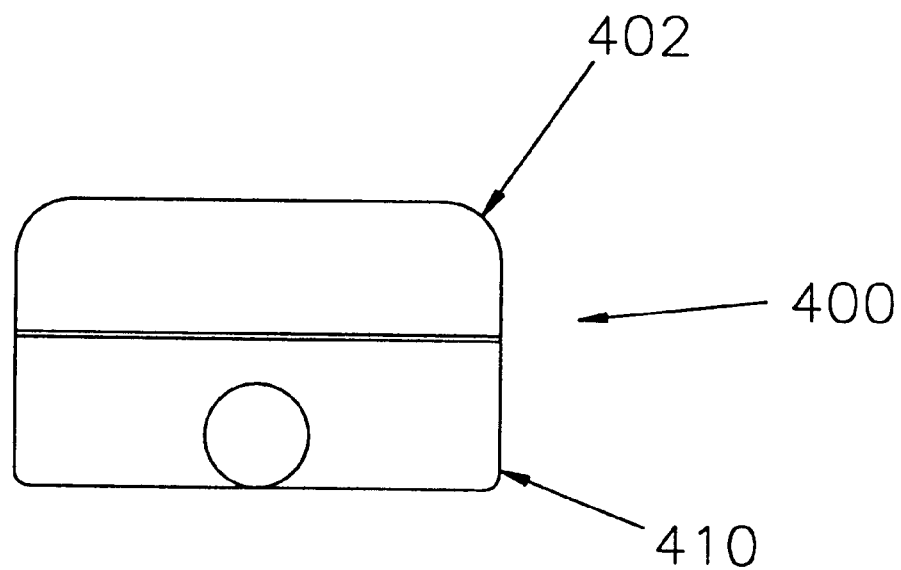
FIG. 9 is a side view of the dam assembly, where the dam assembly has been rotated 90° about its longitudinal axis from the position shown in FIG. 8.
Figure 10:
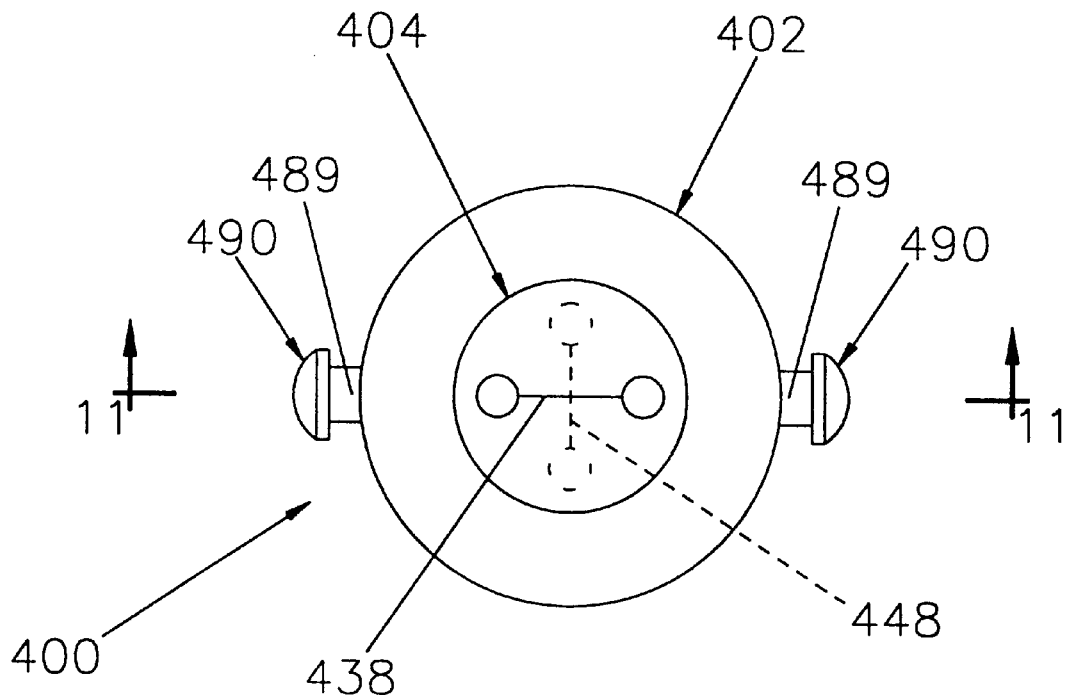
FIG. 10 is a top view of the dam assembly.
Figure 11:
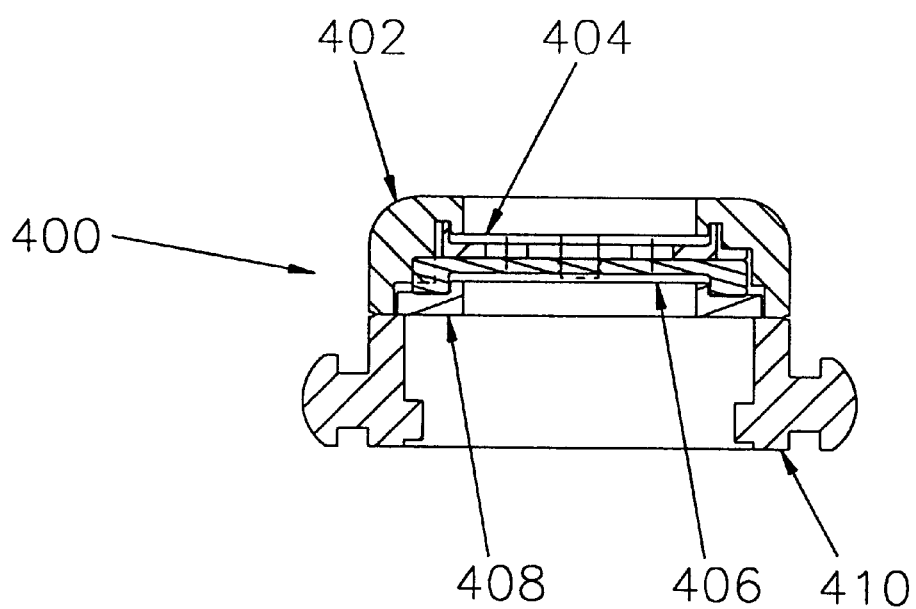
FIG. 11 is a side view, in section, of the dam assembly, as taken along line 11—11 of FIG. 10.
Figure 12:
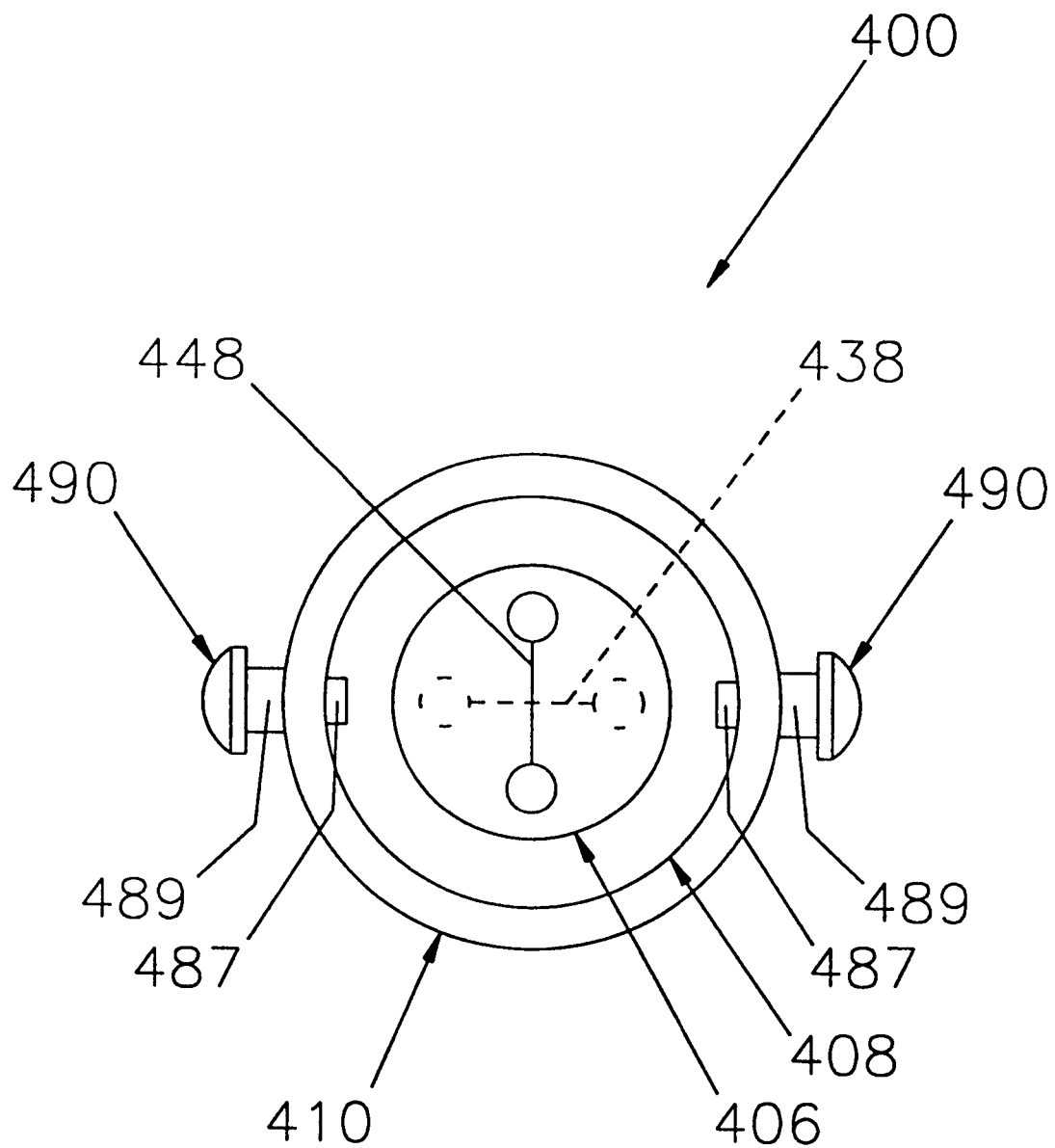
FIG. 12 is a bottom view of the dam assembly.
Figure 13:
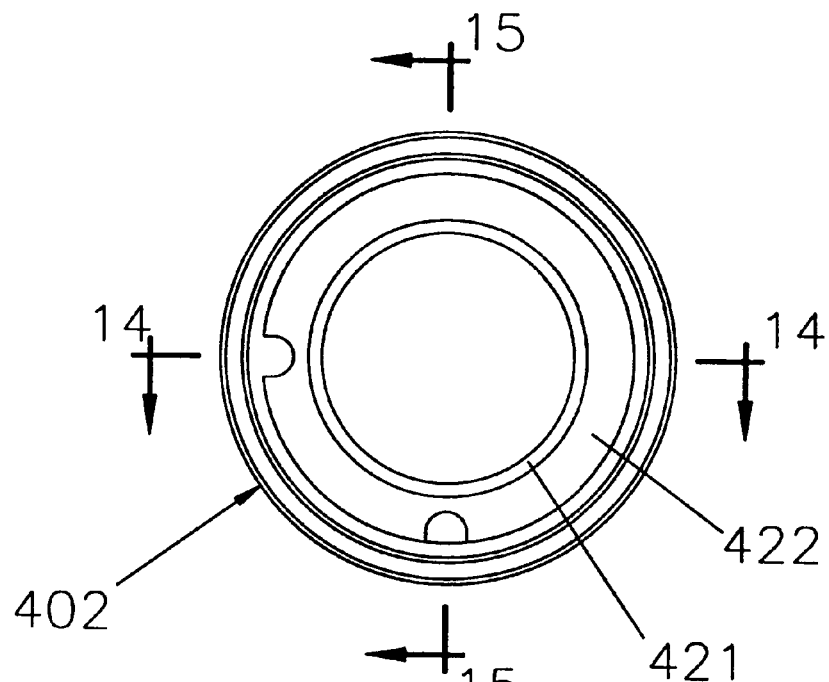
FIG. 13 is a bottom view of the dam assembly's proximal housing member.
Figure 14:
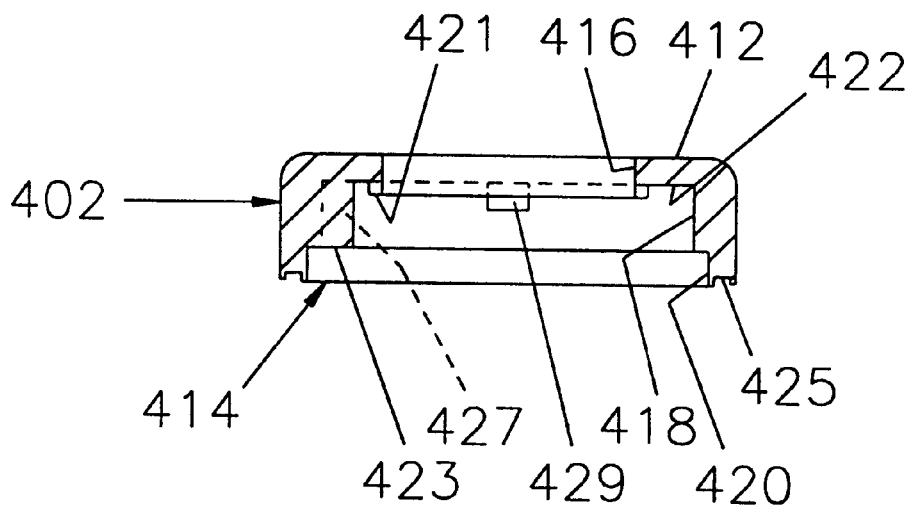
FIG. 14 is a side view, in section, of the dam assembly's proximal housing member, as taken along line 14—14 of FIG. 13, with the proximal housing member's proximal end surface 412 being oriented toward the top of the page.
Figure 15:
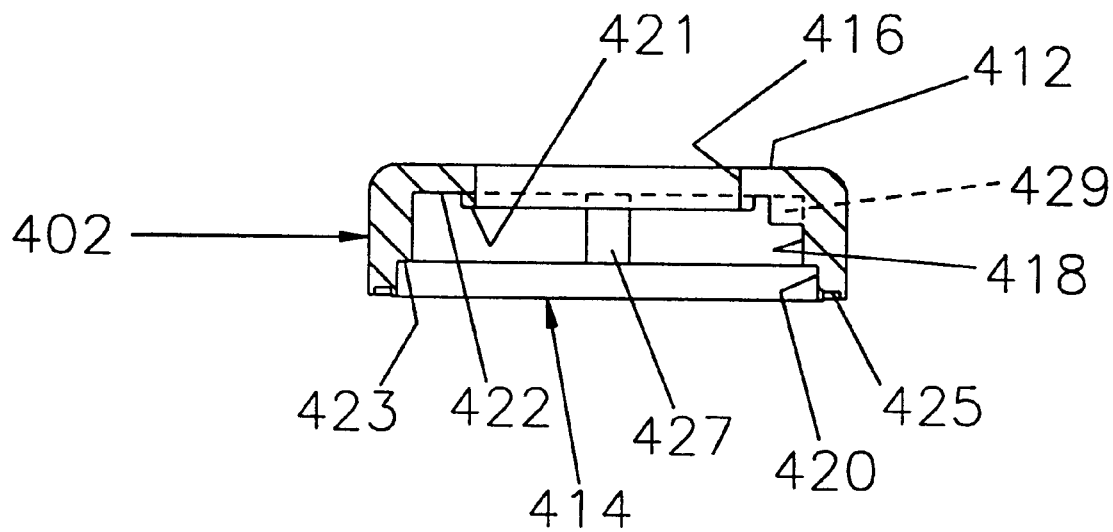
FIG. 15 is a side view, in section, of the dam assembly's proximal housing member, as taken along line 15—15 of FIG. 13, with the proximal housing member's proximal end surface 412 being oriented toward the top of the page.
Figure 16:
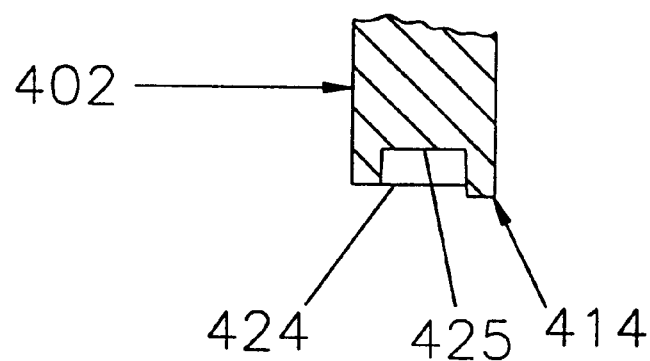
FIG. 16 is an enlarged, partial side view of the lower left hand portion of FIG. 15.

Obturator 300 is also sized so that it can slid on guide rod 100. More particularly, the obturator's central passageway 335 is sized so as to have a diameter which is slightly larger than the diameter of guide rod 100, whereby the obturator can be slipped over the proximal end of guide rod 100 and then slid down the length of the guide rod (see FIG. 7).

Looking next at FIGS. 8–12, dam assembly 400 comprises a proximal housing member 402, a proximal dam member 404, a distal dam member 406, a retaining ring 408, and a distal housing member 410.

Looking now at FIGS. 13–16, proximal housing member 402 comprises a proximal end surface 412, a distal end surface 414, a bore 416, a first counterbore 418, and a second counterbore 420. Bore 416 and first counterbore 418 are coaxial with one another and together define a first shoulder 421. A first annular groove 422 is formed in first shoulder 421. First counterbore 418 and second counterbore 420 are also coaxial with one another and together define a second shoulder 423. Distal end surface 414 is relieved slightly about its periphery, so as to form a step 424 (see FIG. 16). A second annular groove 425 is formed in step 424.

Proximal housing member 402 also comprises a first post 427 and a second post 429. First post 427 extends distally from the floor of first annular groove 422 and terminates flush with second shoulder 423. Second post 429 also extends distally from the floor of first annular groove 422. Second post 429 terminates intermediate first shoulder 421 and second shoulder 423.

Figure 17:
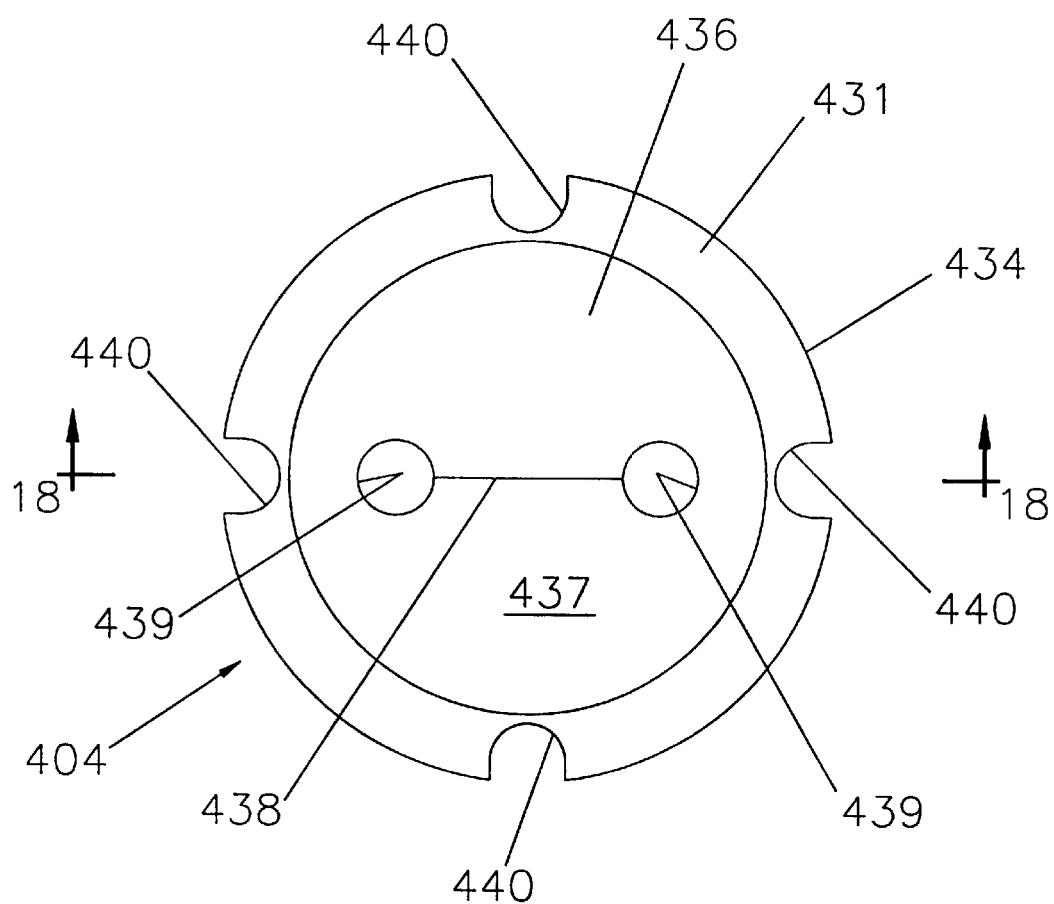
FIG. 17 is a top view of the dam assembly's proximal dam member.
Figure 18:
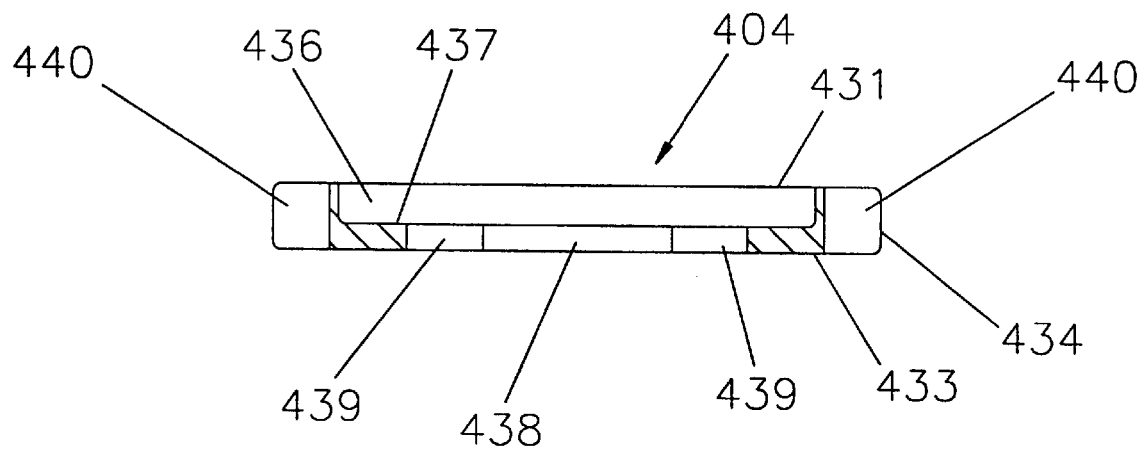
FIG. 18 is a side view, in section, of the dam assembly's proximal dam member, as taken along line 18—18 of FIG. 17, with the proximal dam member's proximal end surface 431 being oriented toward the top of the page.

Looking next at FIGS. 17 and 18, proximal dam member 404 comprises a proximal end surface 431, a distal end surface 433, and a peripheral side surface 434. A central recess 436 is formed in proximal end surface 431. Central recess 436 terminates in a planar floor 437. Proximal dam member 404 also has a slit 438 extending therethrough. Slit 438 is terminated at either end by a relief hole 439. Proximal dam member 404 also comprises four side recesses 440. Each of the side recesses 440 extends radially inwardly from peripheral side surface 434. Each of the side recesses 440 also extends axially between proximal end surface 431 and distal end surface 433.

Figure 19:
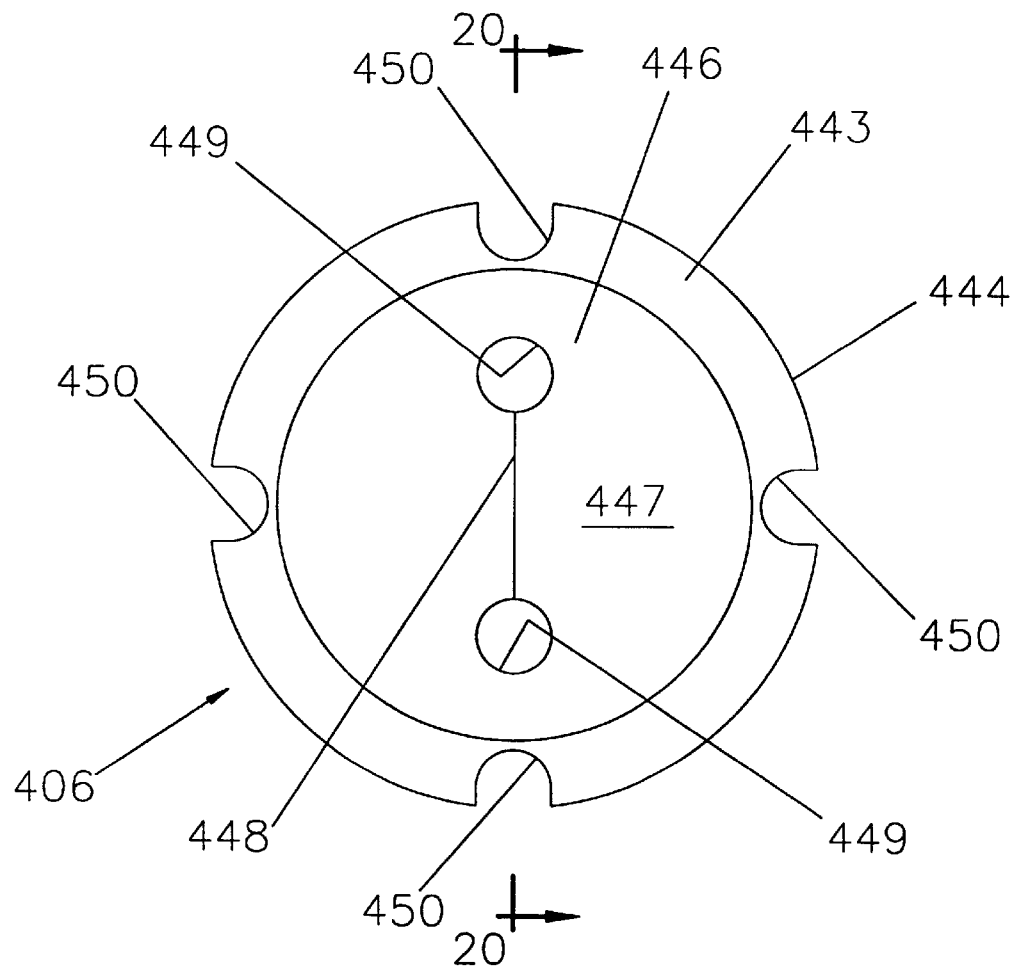
FIG. 19 is a bottom view of the dam assembly's distal dam member.
Figure 20:
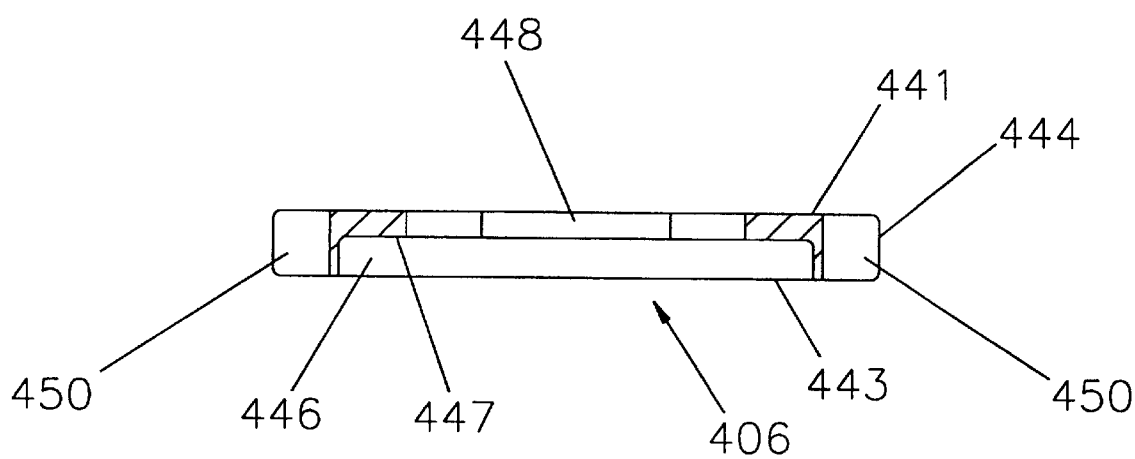
FIG. 20 is a side view, in section, of the dam assembly's distal dam member, as taken along line 20—20 of FIG. 19, with the distal dam member's proximal end surface 441 being oriented toward the top of the page.

Looking next at FIGS. 19 and 20, distal dam member 406 is identical to proximal dam member 404, but is inverted with respect thereto. More particularly, distal dam member 406 comprises a proximal end surface 441, a distal end surface 443, and a peripheral side surface 444. A central recess 446 is formed in distal end surface 443. Central recess 446 terminates in a planar floor 447. Distal dam member 406 also has a slit 448 extending therethrough. Slit 448 is terminated at either end by a relief hole 449. Distal dam member 406 also comprises four side recesses 450. Each of the side recesses 450 extends radially inwardly from peripheral side surface 444. Each of the side recesses 450 also extends axially between proximal end surface 441 and distal end surface 443.

Figure 21:
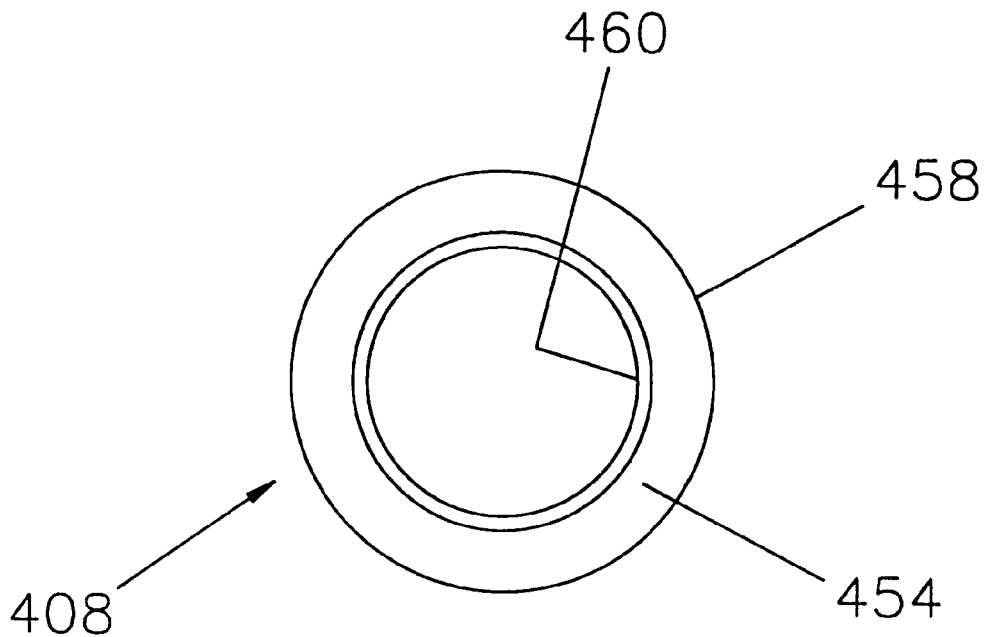
FIG. 21 is a top view of the dam assembly's retaining ring.
Figure 22:
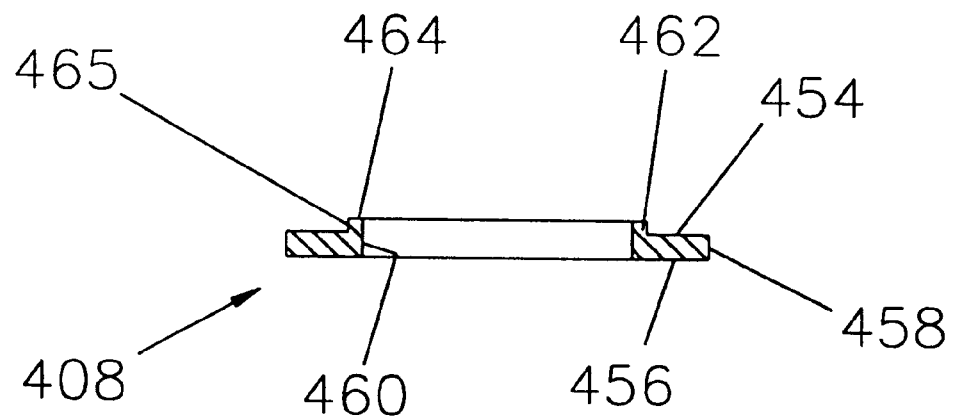
FIG. 22 is a side view, in section, of the dam assembly's retaining ring.

Looking next at FIGS. 21 and 22, retaining ring 408 comprises a proximal end surface 454, a distal end surface 456, and an annular side surface 458. An upraised flange 462, having a proximal end surface 464 and an outer side surface 465, extends proximally from proximal end surface 454. A central bore 460 extends between proximal end surface 464 and distal end surface 456.

Figure 23:
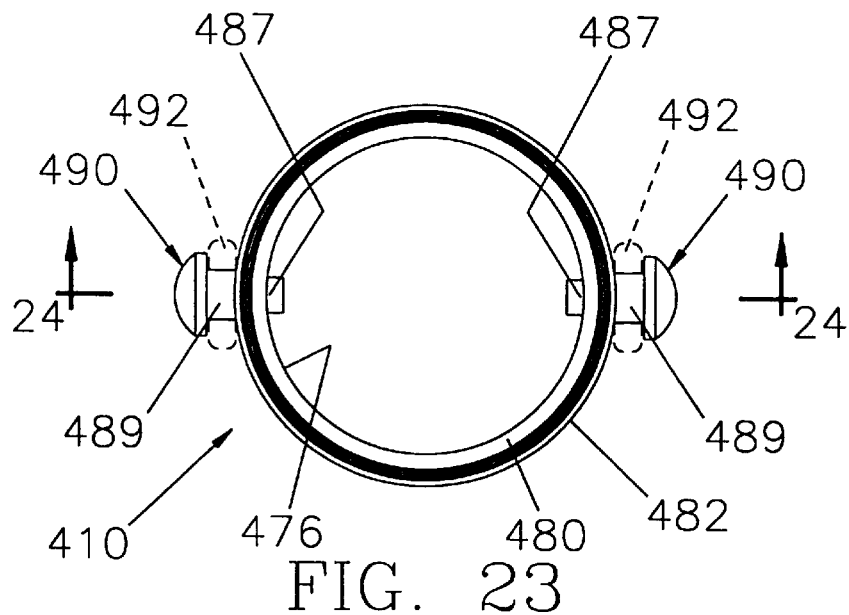
FIG. 23 is a top view of the dam assembly's distal housing member.
Figure 24:
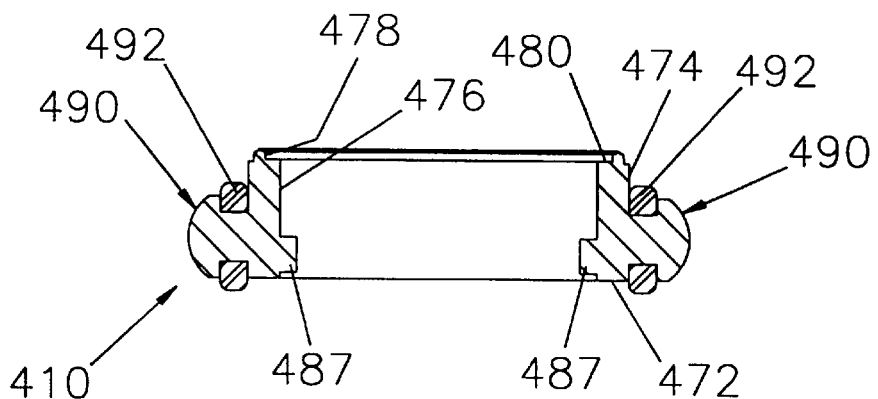
FIG. 24 is a side view, in section, of the dam assembly's distal housing member, as taken along line 24—24 of FIG. 23, with the distal housing member's proximal end being oriented toward the top of the page.
Figure 25:
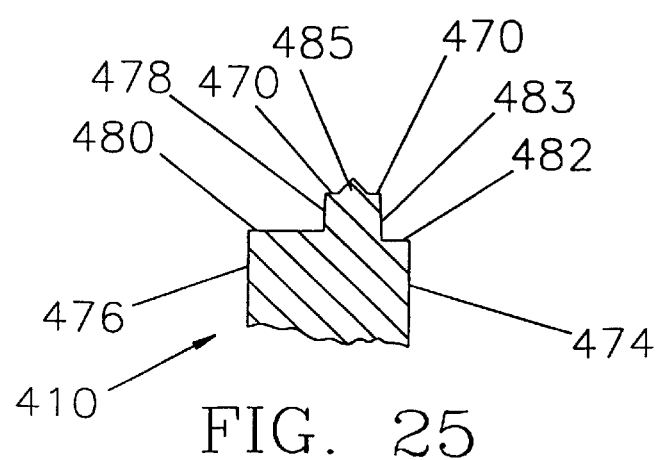
FIG. 25 is an enlarged, partial side view of the upper right hand portion of FIG. 24.

Looking next at FIGS. 23–25, distal housing member 410 comprises a proximal end surface 470, a distal end surface 472, and a peripheral side surface 474. A bore 476 extends proximally from distal end surface 472. A counterbore 478 extends distally from proximal end surface 470. Bore 476 and counterbore 478 are coaxial with one another and together define an annular shoulder 480. The annular edge where proximal end surface 470 and peripheral side surface 474 meet is relieved so as to form an end surface 482 and a side surface 483 (see FIG. 25). Proximal end surface 370 includes an upraised annular ridge 485.

A pair of diametrically opposed mounting pegs 487 project radially into bore 476. A pair of diametrically opposed suture posts 489 project radially out from peripheral side surface 474. Each of the suture posts 489 terminates in an enlarged end cap 490. A resilient rubber grommet 492 is mounted on each of the suture posts 489, between peripheral side surface 474 and end cap 490. Suture posts 489 are aligned with mounting pegs 487, as seen in FIG. 23.

Dam assembly 400 is assembled as follows.

First, proximal dam member 404 is inserted into proximal housing member 402 so that (i) the proximal housing member's first post 427 is received in one of the proximal dam member's side recesses 440 and its second post 429 is received in another of the side recesses 440, (ii) the proximal dam member's slit 438 is aligned with the proximal housing member's first post 427, and (iii) the dam member's proximal surface 431 is in engagement with the floor of the proximal housing member's first annular groove 422.

Next, distal dam member 406 is inserted into proximal housing member 402 so that (i) the proximal housing member's first post 427 is received in one of the distal dam member's side recesses 450 and its second post 429 is aligned with another of the side recesses 450, (ii) the distal dam member's slit 448 extends perpendicular to the proximal dam member's slit 438, and (iii) the distal dam member's proximal end surface 441 is in engagement with the proximal dam member's distal end surface 433.

Then retaining ring 408 is inserted into proximal housing member 402 so that (i) the retaining ring's upraised flange 462 is received in the distal dam member's central recess 446, (ii) the retaining ring's end surface 464 engages the dam member's planar floor 447, and (iii) the retaining ring's proximal surface 454 engages the distal dam member's distal end surface 443.

Next, distal housing member 410 is joined with proximal housing member 402 so that (i) the distal housing member's upraised annular ridge 485 extends into (and contacts the floor of) the proximal housing member's second annular groove 425, (ii) the distal housing member's annular shoulder 480 engages the proximal housing member's distal end surface 414, and (iii) the distal housing member's two mounting pegs 487 are aligned with the proximal dam member's slit 438. As this occurs, the distal housing member's annular shoulder 480 may lightly contact the retaining ring's distal end surface 456. Then proximal housing member 402 and distal housing member 404 are securely attached to one another, e.g. by ultrasonic welding. Attachment is effected so that retaining ring 408 is not fixed or fastened to either proximal housing member 402 or distal housing member 406.

Dam assembly 400 is sized so that it can be mounted on proximal portion 215 of cannula housing 200. More particularly, dam assembly 400 is sized so that (i) the distal housing member's bore 476 will make a close sliding fit with the outer surface of the cannula housing's proximal portion 215, (ii) the distal housing member's mounting pegs 487 will make a close sliding fit with the cannula housing's L-shaped grooves 235, and (iii) the housing member's proximal end surface 220 will engage the retaining ring's distal end surface 456 before the housing member's mounting pegs 487 engage the distal ends of the grooves' longitudinally extending lengths 240.

On account of this construction, dam assembly 400 can be mounted on proximal portion 215 of cannula housing 200 as follows.

Figure 26:
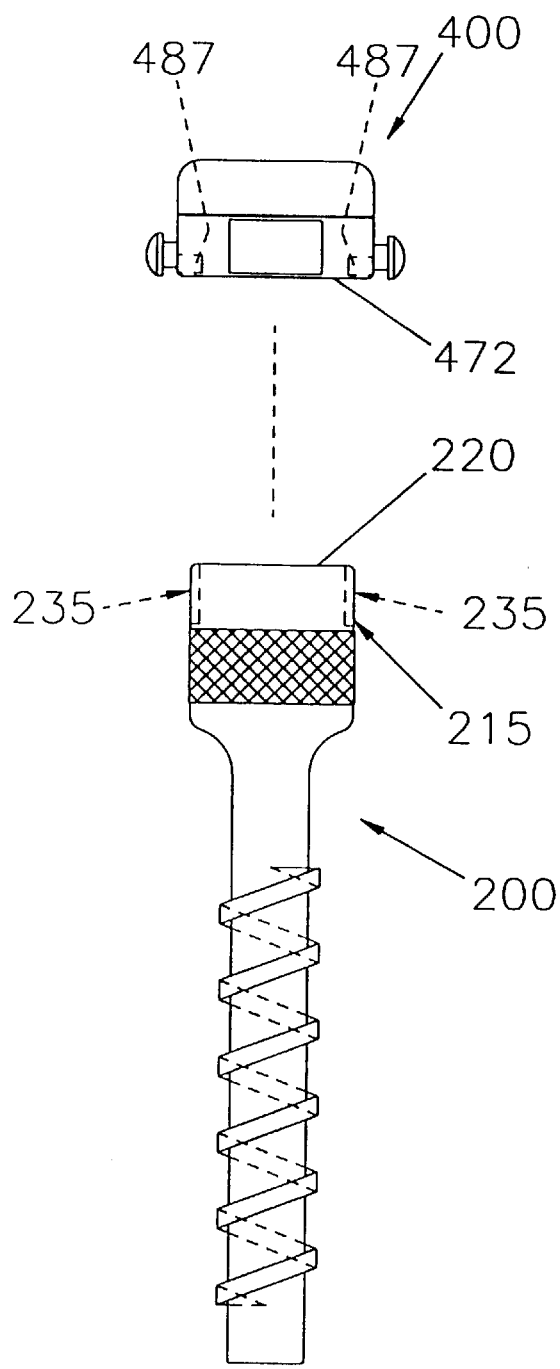
FIG. 26 is a side view showing the dam assembly about to be mounted to the cannula housing.
Figure 27:
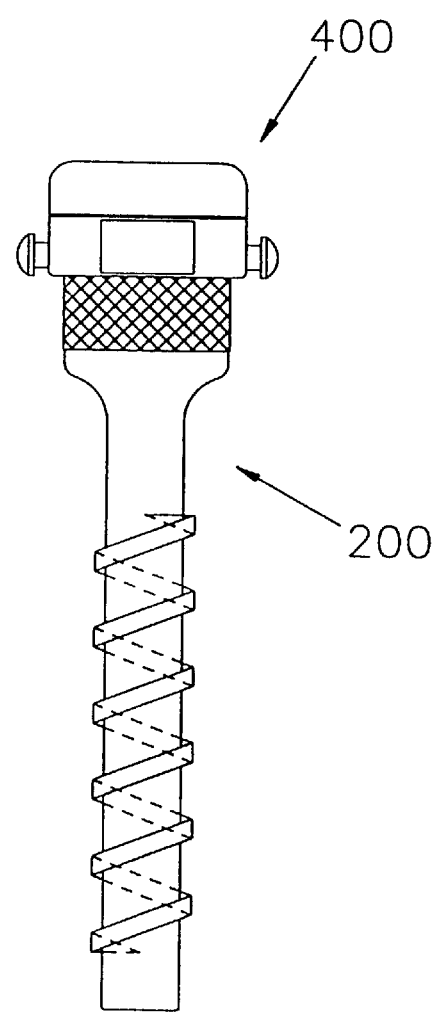
FIG. 27 is a side view showing the dam assembly mounted to the cannula housing.

First, dam assembly 400 is positioned adjacent to cannula housing 200 so that the dam assembly's distal end surface 472 is adjacent to the cannula housing's proximal end surface 220, and so that the dam assembly's mounting pegs 487 are aligned with the longitudinally extending lengths 240 of the cannula housing's L-shaped grooves 235 (see FIG. 26). Next, dam assembly 400 is forced over the housing assembly's proximal portion 215 so that mounting pegs 487 move down the longitudinally extending lengths 240 of L-shaped grooves 235. As mounting pegs 287 near the distal ends of longitudinally extending lengths 240, the cannula housing's proximal end surface 220 engages the retaining ring's distal end surface 456. Dam assembly 400 is pushed further towards cannula housing 200 until mounting pegs 287 engage the distal ends of longitudinally extending lengths 240. This will cause retaining ring 408 to axially compress the two resilient dam members 404, 406 somewhat. Then dam assembly 400 is rotated so as to bring mounting pegs 287 along the circumferentially extending lengths 245 of mounting grooves 235. Dam assembly 400 is rotated far enough so that mounting pegs 287 slip past lips 250. Then dam assembly 400 is released. At this point the two resilient dam members 404, 406 will urge dam assembly 400 away from cannula housing 200, whereby the interaction of mounting pegs 287 with lips 250 will prevent dam assembly 400 from becoming accidentally detached from cannula housing 200 (see FIG. 27). Dam assembly 400 may, of course, be deliberately detached from cannula housing 200 by simply reversing the foregoing procedure.

The new surgical cannula system is used as follows.

Figure 28:
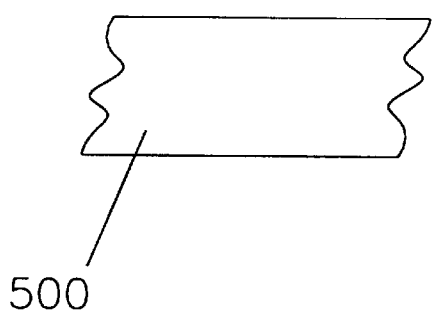
FIG. 28 is an illustrative side view showing a piece of tissue.
Figure 29:
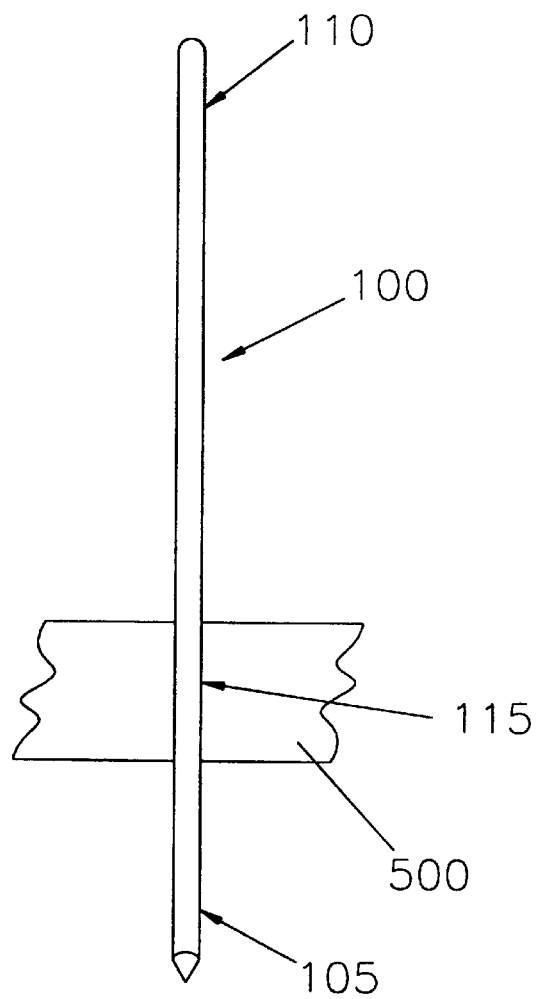
FIG. 29 is an illustrative side view showing the guide rod extending through the tissue.

First, guide rod 100 is inserted into the patient so that the guide rod's distal portion 105 is located at an interior surgical site, its proximal portion 110 is located outside the patient, and its shaft 115 extends through all intervening tissue 500 (see generally FIGS. 28 and 29).

Figures 30, 31:
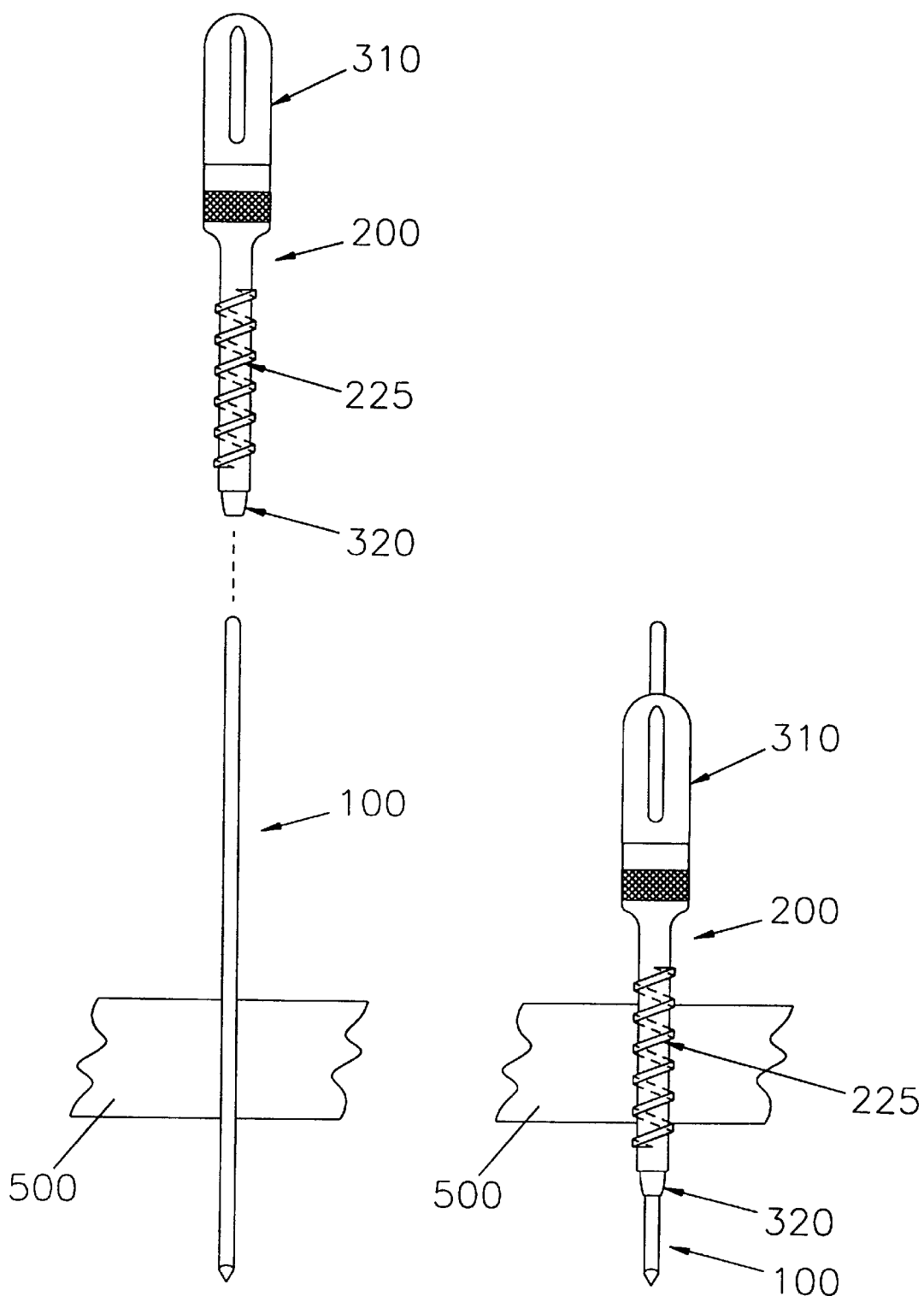
FIG. 30 is an illustrative side view showing the guide rod extending through the tissue, and the obturator inserted into the cannula housing, with that assembly about to be mounted onto the guide rod.
FIG. 31 is a view like that of FIG. 30, except that the cannula housing and obturator have been moved down the guide rod as a unit so that the distal ends of the obturator and cannula housing have passed completely through the tissue, with the cannula housing's helical thread securely engaging the tissue.

Next, obturator 300 is assembled to cannula housing 200 by inserting obturator 300 into the cannula housing's central passageway 260 and screwing the obturator's threaded intermediate portion 315 into the cannula housing's threaded counterbore 270. As this occurs, the obturator's frustoconical distal tip 320 will exit from the distal end of the cannula housing, and the obturator's handle 310 will come to rest adjacent to the cannula housing's proximal portion 215. Next, the surgeon fits this assembly over the proximal end of the guide rod and slides the entire assembly down the guide rod as a unit until the obturator's frustoconical distal tip 320 comes into engagement with tissue 500. Then the surgeon forces the assembly through tissue 500, twisting the assembly as it penetrates the tissue so that the cannula housing's helical thread 225 will set securely into the tissue (see generally FIGS. 30 and 31).

At this point, obturator 300 is unscrewed from cannula housing 200, and then it is withdrawn from cannula housing 200 and guide rod 100 (see generally FIG. 32). Next, guide rod 100 is also removed from the patient, leaving only cannula housing 200 extending through tissue 500 (see generally FIG. 33).

Figure 34:
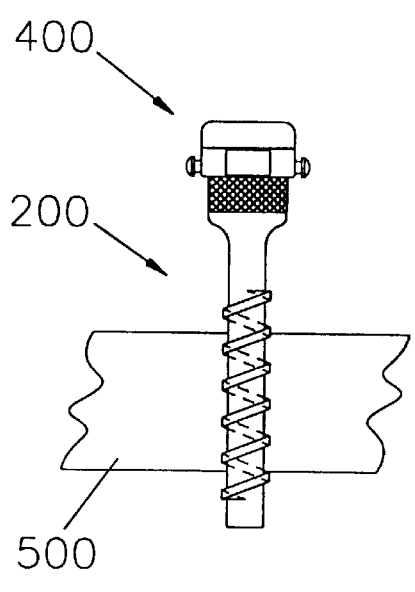
FIG. 34 is a view like that of FIG. 33, except that the dam assembly has been mounted to the cannula housing.

Next, dam assembly 400 is mounted to the proximal end of cannula housing 200. This is done by aligning the dam assembly's mounting pegs 487 with lengths 240 of the cannula housing's two L-shaped grooves 235, moving the dam assembly into engagement with the cannula housing, and then turning the dam assembly relative to the housing so as to lock the dam assembly to the cannula housing (see generally FIG. 34).

At this point the cannula is ready for use by the surgeon. During such use, it is contemplated that the interior surgical site will be inflated and/or irrigated with a fluid (e.g. with a liquid during arthroscopic surgery and a gas during laparoscopic surgery). This fluid will be inhibited from leaving the surgical site through the cannula, due to the presence of the two dam members 404, 406. More particularly, when no instrument is inserted through the cannula, dam members 404, 406 will lie flat against one another and their slits will remain substantially closed, so that little fluid will be able to pass by the dam members. Alternatively, when a surgical instrument or other object extends through the cannula, the instrument will pass through the dam slits 438, 448, and the resilient dam members 404, 406 will close about those instruments, so as to form a fairly tight seal about the instruments. As a result, relatively little fluid will be able to pass by the dam members. Furthermore, by orienting dam member 404, 406 so that their slits 438, 448 extend perpendicular to one another, the two dam members will be able to cooperate with one another so as to achieve a superior seal about any surgical instrument (or other object) which may extend through the cannula.

Figure 35:
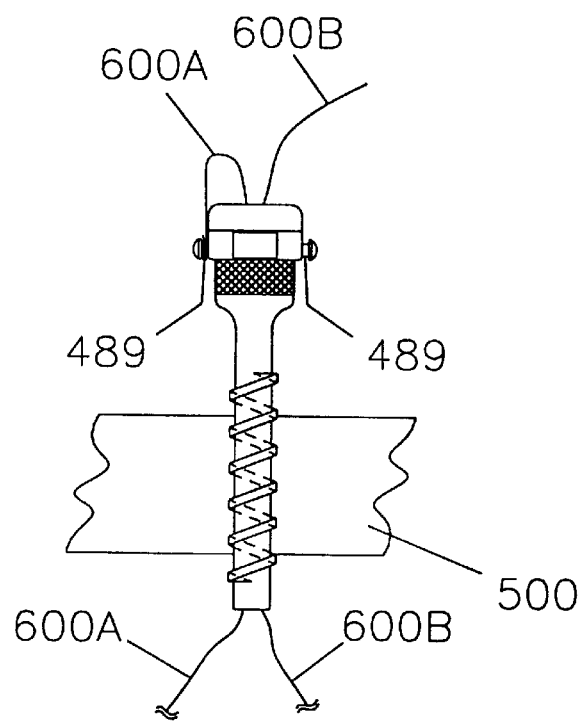
FIG. 35 is a view like that of FIG. 34, except that two lengths of suture are shown extending through the cannula housing and dam assembly, with one of the lengths of suture being attached to one of the dam assembly's suture posts.

During use, it is also contemplated that one or more sutures may extend through the cannula. In the case where at least two sutures are involved, it is generally desirable to keep these sutures separate and distinct from one another, without any tangling. In addition, it is also generally desirable for the surgeon to be able to readily distinguish one suture from another, when viewing only the proximal ends of the sutures extending out of the cannula. To this end, the present invention provides the suture posts 489. More particularly, as seen in FIG. 35, the surgeon can secure the proximal end of one suture 600A to one of the suture posts 489 so as to keep it separate and distinct from another suture 600B (which may or may not be secured to the other suture post 489 during the surgical procedure). In this respect it will also be appreciated that the end caps 490 and grommets 492 will permit suture ends to be quickly and easily secured to the suture posts 489, by providing a ready interference fit.

In this respect it should also be appreciated that by orienting dam members 404, 406 so that the proximal slit 438 is aligned with suture posts 489 and distal slit 448 extends transverse to suture posts 489, dam assembly 400 will be able to make a superior seal about any sutures fastened to the suture posts. More particularly, any sutures emerging from the cannula and being secured to suture posts 489 will be able to separate along the length of proximal slit 438, rather than transverse to it. As a result, these suture can be secured to suture posts 489 in a fairly taut condition, without pulling the flaps of proximal dam member 404 apart. Furthermore, while it is true that the separation of the sutures will extend transverse to the length of distal slit 448, and hence tend to pull the flaps of distal dam member 406 apart, these flaps will be kept fairly planar by the presence of the proximal dam member 404. Hence dam assembly 400 will be able to make fairly good seal about any sutures extending through the cannula, even when those sutures are secured to suture posts 489.

It will, of course, be appreciated that numerous changes may be made to the preferred embodiment disclosed above without departing from the scope of the present invention. Thus, for example, the screw arrangement used to mount obturator 300 to cannula housing 200 could be replaced by some equivalent mounting means, e.g. a bayonet mount. Furthermore, the bayonet mount used to mount dam assembly 400 to cannula housing 200 could be replaced by some equivalent mounting means, e.g. a screw mount. These and other changes of their type are considered to be within the scope of the present invention.

What is claimed is:

1. A method of deploying a surgical cannula in tissue comprising:

(1) providing:
- a guide rod comprising a shaft having a distal end and a proximal end;
- a cannula housing comprising a distal end, a proximal end, and a central passageway extending therebetween, said cannula housing further comprising first and second mount receiving means and including tissue locking means on an exterior surface thereof;
- an obturator comprising a shaft having a distal end, a proximal end, and a central passageway extending therebetween, said obturator further comprising first mounting means for releasably attaching to said first mount receiving means, said obturator being sized so that said distal end thereof projects out said distal end of said cannula housing when said first mounting means are in operative engagement with said first mount receiving means; and
- a dam assembly comprising a housing, sealing means disposed in said housing, and second mounting means for operatively engaging said second mount receiving means so as to sealably mount said dam assembly to said cannula housing, said dam assembly further comprising suture holding means for separately and distinctly securing a plurality of suture ends to said dam assembly;

(2) inserting said guide rod into a patient so that said distal end thereof is located at an interior surgical site, said proximal end thereof is located outside said patient, and said shaft extends through all intervening tissue;

(3) assembling said obturator to said cannula housing by inserting said obturator into said cannula housing's central passageway so as to cause said first mounting means to operatively engage said first mount receiving means, thereby releasably attaching said obturator to said cannula housing so that said obturator's distal end projects out said distal end of said cannula housing and said obturator's proximal end projects out said proximal end of said cannula housing;

(4) fitting said obturator/cannula housing assembly over said proximal end of said guide rod;

(5) sliding said obturator/cannula housing assembly down said guide rod as a unit until said obturator's distal end comes into engagement with said tissue;

(6) forcing said obturator/cannula housing assembly through said tissue so that said distal end of said assembly penetrates said tissue and said cannula housing's tissue locking means securely engage said tissue;

(7) detaching said obturator from said cannula housing;

(8) withdrawing said obturator from said cannula housing and said guide rod;

(9) withdrawing said guide rod from said patient, thus leaving only said proximal portion of said cannula housing extending through said tissue; and

(10) assembling said dam assembly to said cannula housing by bringing said dam assembly against said cannula housing so that said dam assembly's second mounting means operatively engage said cannula housing's second mounting means, thus sealing said cannula housing's central passageway with said dam assembly's sealing means.

2. A method according to claim 1 further comprising the steps of:

(11) deploying at least one suture through said cannula housing and through said sealing means so as to have at least one proximal suture end extending outwardly from said dam assembly; and

(12) releaseably attaching said at least one proximal suture end to said suture holding means.

* * * * *